US007011095B2

(12) United States Patent
Wolf et al.

(10) Patent No.: US 7,011,095 B2
(45) Date of Patent: Mar. 14, 2006

(54) VALVE DESIGNS FOR LEFT VENTRICULAR CONDUITS

(75) Inventors: Scott J. Wolf, Minneapolis, MN (US);
Peter J. Wilk, New York, NY (US);
Nancy M. Briefs, Nashua, NH (US)

(73) Assignee: Percardia, Inc., Merrimack, NH (US)

( * ) Notice: Subject to any disclaimer, the term of this patent is extended or adjusted under 35 U.S.C. 154(b) by 0 days.

(21) Appl. No.: 10/463,798

(22) Filed: Jun. 18, 2003

(65) Prior Publication Data

US 2003/0216679 A1   Nov. 20, 2003

Related U.S. Application Data

(63) Continuation of application No. 09/368,393, filed on Aug. 4, 1999, now Pat. No. 6,641,610.

(60) Provisional application No. 60/099,777, filed on Sep. 10, 1998.

(51) Int. Cl.
*A61F 2/06* (2006.01)
*A61B 17/08* (2006.01)

(52) U.S. Cl. .................... 128/898; 606/153

(58) Field of Classification Search ............... 623/1.11, 623/1.12, 1.36, 1.42–1.46; 606/153, 191, 606/192–194, 198, 151, 152; 604/8, 9; 600/16–18; 128/898
See application file for complete search history.

(56) References Cited

U.S. PATENT DOCUMENTS

| | | |
|---|---|---|
| 3,671,979 A | 6/1972 | Moulopoulos |
| 3,858,246 A | 1/1975 | Milo |
| 3,911,502 A | 10/1975 | Boretos |
| 3,926,215 A | 12/1975 | Macleod |
| 4,441,215 A | 4/1984 | Kaster |
| 4,503,568 A | 3/1985 | Madras |
| 4,655,773 A | 4/1987 | Grassi |
| 4,680,031 A | 7/1987 | Alonso |
| 4,733,665 A | 3/1988 | Palmaz |
| 4,769,029 A | 9/1988 | Patel |
| 4,953,553 A | 9/1990 | Tremulis |
| 4,979,955 A | 12/1990 | Smith |
| 4,995,857 A | 2/1991 | Arnold |
| 5,035,702 A | 7/1991 | Taherei |
| 5,135,467 A | 8/1992 | Citron |
| 5,193,546 A | 3/1993 | Shaknovich |
| 5,258,008 A | 11/1993 | Wilk |
| 5,287,861 A | 2/1994 | Wilk |

(Continued)

FOREIGN PATENT DOCUMENTS

AU            757647         8/1999

(Continued)

OTHER PUBLICATIONS

Anne Bohning, Kenneth Jochim & Louis N. Katz; "The Thebesian Vessels as a Source of Nourishment for the Myocardium"; American Journal of Physiology; 1933; pp. 183-200; vol. 106; American Physiological Society; U.S.A.

(Continued)

*Primary Examiner*—David J. Isabella
(74) *Attorney, Agent, or Firm*—Finnegan, Henderson, Farabow, Garrett & Dunner LLP

(57) ABSTRACT

Disclosed is a conduit that provides a bypass around a stenosis or occlusion in a coronary artery. The conduit is adapted to be positioned in the myocardium to provide a passage for blood to flow from a heart chamber to a coronary artery, at a site distal to the blockage or stenosis in the coronary artery. The conduit has a one-way valve positioned therein to prevent the backflow of blood from the coronary artery into the heart chamber.

50 Claims, 8 Drawing Sheets

U.S. PATENT DOCUMENTS

| | | |
|---|---|---|
| 5,330,486 A | 7/1994 | Wilk |
| 5,332,402 A | 7/1994 | Teitelbaum |
| 5,344,426 A | 9/1994 | Lau et al. |
| 5,385,541 A | 1/1995 | Kirsch et al. |
| 5,389,096 A | 2/1995 | Aita et al. |
| 5,397,351 A | 3/1995 | Pavcnik |
| 5,409,019 A | 4/1995 | Wilk |
| 5,411,552 A | 5/1995 | Andersen et al. |
| 5,423,744 A | 6/1995 | Gincheff et al. |
| 5,423,851 A | 6/1995 | Samuels |
| 5,429,144 A * | 7/1995 | Wilk .......................... 128/898 |
| 5,443,497 A | 8/1995 | Venbrux |
| 5,456,712 A | 10/1995 | Maginot |
| 5,456,714 A | 10/1995 | Owen |
| 5,470,320 A | 11/1995 | Tiefenbrun et al. |
| 5,487,760 A | 1/1996 | Villafana |
| 5,500,014 A | 3/1996 | Quijano et al. |
| 5,527,337 A | 6/1996 | Stack et al. |
| 5,554,119 A | 9/1996 | Harrison et al. |
| 5,554,185 A | 9/1996 | Block et al. |
| 5,571,215 A | 11/1996 | Sterman et al. |
| 5,578,075 A | 11/1996 | Dayton |
| 5,593,434 A | 1/1997 | Williams |
| 5,609,626 A | 3/1997 | Quijano et al. |
| 5,618,299 A | 4/1997 | Khosravi et al. |
| 5,655,548 A | 8/1997 | Nelson et al. |
| 5,662,124 A | 9/1997 | Wilk |
| 5,713,950 A | 2/1998 | Cox |
| 5,733,267 A | 3/1998 | Toro |
| 5,755,682 A | 5/1998 | Knudson et al. |
| 5,758,663 A | 6/1998 | Wilk et al. |
| 5,797,933 A | 8/1998 | Snow et al. |
| 5,807,384 A | 9/1998 | Mueller |
| 5,810,836 A | 9/1998 | Hussein et al. |
| 5,824,038 A | 10/1998 | Wall |
| 5,824,071 A | 10/1998 | Nelson et al. |
| 5,830,222 A | 11/1998 | Makower |
| 5,840,081 A | 11/1998 | Andersen et al. |
| 5,843,163 A | 12/1998 | Wall |
| 5,851,232 A | 12/1998 | Lois |
| 5,855,597 A | 1/1999 | Jayaraman |
| 5,865,723 A | 2/1999 | Love |
| 5,876,373 A | 3/1999 | Giba et al. |
| 5,876,419 A | 3/1999 | Carpenter et al. |
| 5,878,751 A | 3/1999 | Hussein et al. |
| 5,885,259 A | 3/1999 | Berg |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,931,868 A | 8/1999 | Gross |
| 5,935,119 A | 8/1999 | Guy et al. |
| 5,935,161 A | 8/1999 | Robinson et al. |
| 5,935,162 A | 8/1999 | Dang |
| 5,938,632 A | 8/1999 | Ellis |
| 5,944,019 A | 8/1999 | Knudson et al. |
| 5,961,548 A | 10/1999 | Schmulewitz |
| 5,968,064 A | 10/1999 | Selmon et al. |
| 5,968,093 A | 10/1999 | Kranz |
| 5,971,993 A | 10/1999 | Hussein et al. |
| 5,976,155 A | 11/1999 | Foreman et al. |
| 5,976,159 A | 11/1999 | Bolduc et al. |
| 5,976,169 A | 11/1999 | Imran |
| 5,976,181 A | 11/1999 | Whelan et al. |
| 5,976,182 A | 11/1999 | Cox |
| 5,976,192 A | 11/1999 | McIntyre et al. |
| 5,976,650 A | 11/1999 | Campbell et al. |
| 5,979,455 A | 11/1999 | Maginot |
| 5,980,533 A | 11/1999 | Holman |
| 5,980,548 A * | 11/1999 | Evans et al. ................. 606/185 |
| 5,980,551 A | 11/1999 | Summers et al. |
| 5,980,552 A | 11/1999 | Pinchasik et al. |
| 5,980,553 A | 11/1999 | Gray et al. |
| 5,980,566 A | 11/1999 | Alt et al. |
| 5,980,570 A | 11/1999 | Simpson |
| 5,984,955 A | 11/1999 | Wisselink |
| 5,984,956 A | 11/1999 | Tweden et al. |
| 5,984,963 A | 11/1999 | Ryan et al. |
| 5,984,965 A | 11/1999 | Knapp et al. |
| 5,989,207 A | 11/1999 | Hughes |
| 5,989,287 A | 11/1999 | Yang et al. |
| 5,993,481 A | 11/1999 | Marcade et al. |
| 5,993,482 A | 11/1999 | Chuter |
| 5,997,525 A | 12/1999 | March et al. |
| 5,997,563 A | 12/1999 | Kretiers |
| 5,997,573 A | 12/1999 | Quijano et al. |
| 5,999,678 A | 12/1999 | Murphy-Chutorian et al. |
| 6,001,123 A | 12/1999 | Lau |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,007,575 A | 12/1999 | Samuels |
| 6,007,576 A | 12/1999 | McClellan |
| 6,010,449 A | 1/2000 | Selmon et al. |
| 6,010,530 A | 1/2000 | Goicoechea |
| 6,017,365 A | 1/2000 | Von Oepen |
| 6,026,814 A | 2/2000 | LaFontaine et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,045,565 A | 4/2000 | Ellis et al. |
| 6,053,911 A | 4/2000 | Ryan et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,095,997 A | 8/2000 | French et al. |
| 6,102,941 A | 8/2000 | Tweden et al. |
| 6,106,538 A | 8/2000 | Shiber |
| 6,110,201 A | 8/2000 | Quijano et al. |
| 6,113,630 A | 9/2000 | Vanney et al. |
| 6,113,823 A | 9/2000 | Eno |
| 6,117,165 A | 9/2000 | Becker |
| 6,120,520 A | 9/2000 | Saadat et al. |
| 6,123,682 A | 9/2000 | Knudson et al. |
| 6,126,649 A | 10/2000 | VanTassel et al. |
| 6,126,654 A | 10/2000 | Giba et al. |
| 6,132,451 A | 10/2000 | Payne et al. |
| 6,139,541 A | 10/2000 | Vanney et al. |
| 6,152,141 A | 11/2000 | Stevens et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,162,245 A | 12/2000 | Jayaraman |
| 6,165,185 A | 12/2000 | Shennib et al. |
| 6,165,188 A | 12/2000 | Saadat et al. |
| 6,168,614 B1 | 1/2001 | Andersen et al. |
| 6,171,251 B1 | 1/2001 | Mueller et al. |
| 6,182,668 B1 | 2/2001 | Tweden et al. |
| 6,186,972 B1 | 2/2001 | Nelson et al. |

| Patent No. | Date | Inventor |
|---|---|---|
| 6,187,034 B1 | 2/2001 | Frantzen |
| 6,190,353 B1 | 2/2001 | Makower et al. |
| 6,193,726 B1 | 2/2001 | Vanney |
| 6,193,734 B1 | 2/2001 | Bolduc et al. |
| D438,618 S | 3/2001 | Solem |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,203,556 B1 | 3/2001 | Evans et al. |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,245,102 B1 | 6/2001 | Jayaraman |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,719 B1 | 9/2001 | Garberoglio |
| 6,290,728 B1 | 9/2001 | Phelps et al. |
| 6,293,955 B1 | 9/2001 | Houser et al. |
| 6,302,875 B1 | 10/2001 | Makower et al. |
| 6,302,892 B1 | 10/2001 | Wilk |
| 6,306,125 B1 | 10/2001 | Parker et al. |
| 6,322,548 B1 | 11/2001 | Payne et al. |
| 6,330,884 B1 | 12/2001 | Kim |
| 6,350,248 B1 | 2/2002 | Knudson et al. |
| 6,361,519 B1 | 3/2002 | Knudson et al. |
| 6,363,938 B1 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B1 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B1 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B1 | 9/2002 | Gambale et al. |
| 6,447,539 B1 | 9/2002 | Nelson et al. |
| 6,454,760 B1 | 9/2002 | Vanney |
| 6,454,794 B1 | 9/2002 | Knudson et al. |
| 6,458,092 B1 | 10/2002 | Gambale et al. |
| 6,458,140 B1 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B1 | 11/2002 | Herweck et al. |
| 6,482,220 B1 | 11/2002 | Mueller |
| 6,491,689 B1 | 12/2002 | Ellis et al. |
| 6,491,707 B1 | 12/2002 | Makower et al. |
| 6,508,825 B1 | 1/2003 | Selmon et al. |
| 6,511,458 B1 | 1/2003 | Milo et al. |
| 6,514,217 B1 | 2/2003 | Selmon et al. |
| 6,514,271 B1 | 2/2003 | Evans et al. |
| 6,517,527 B1 | 2/2003 | Gambale et al. |
| 6,517,558 B1 | 2/2003 | Gittings et al. |
| 6,524,323 B1 | 2/2003 | Nash et al. |
| 6,544,230 B1 | 4/2003 | Flaherty |
| 6,559,132 B1 | 5/2003 | Holmer |
| 6,561,998 B1 | 5/2003 | Roth et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,575,168 B1 | 6/2003 | LaFontaine et al. |
| 6,579,311 B1 | 6/2003 | Makower |
| 6,582,444 B1 | 6/2003 | Wilk |
| 6,599,304 B1 | 7/2003 | Selmon et al. |
| 6,605,053 B1 | 8/2003 | Kamm et al. |
| 6,605,113 B1 | 8/2003 | Wilk |
| 6,610,100 B1 | 8/2003 | Phelps et al. |
| 6,613,081 B1 | 9/2003 | Kim et al. |
| 6,616,675 B1 | 9/2003 | Evard et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B1 | 11/2003 | Wolf et al. |
| 6,651,670 B1 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,669,709 B1 | 12/2003 | Cohn et al. |
| 6,685,648 B1 | 2/2004 | Flaherty et al. |
| 6,694,983 B1 | 2/2004 | Wolf et al. |
| 6,709,425 B1 | 3/2004 | Gambale et al. |
| 6,709,444 B1 | 3/2004 | Makower |
| 6,719,770 B1 | 4/2004 | Laufer et al. |
| 6,726,677 B1 | 4/2004 | Flaherty et al. |
| 6,746,464 B1 | 6/2004 | Makower |
| 6,774,278 B1 | 8/2004 | Ragheb et al. |
| 6,786,929 B1 | 9/2004 | Gambale et al. |
| 6,802,858 B1 | 10/2004 | Gambale et al. |
| 6,808,498 B1 | 10/2004 | Laroya et al. |
| 6,830,568 B1 | 12/2004 | Kesten et al. |
| 6,863,684 B1 | 3/2005 | Kim et al. |
| 6,881,199 B1 | 4/2005 | Wilk et al. |
| 2001/0000041 A1 | 3/2001 | Selmon et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |

| | | |
|---|---|---|
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0047197 A1 | 11/2001 | Foley |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0033180 A1 | 3/2002 | Solem |
| 2002/0045928 A1 | 4/2002 | Boekstegers |
| 2002/0049486 A1 | 4/2002 | Knudson et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0077566 A1 | 6/2002 | Laroya et al. |
| 2002/0077654 A1 | 6/2002 | Javier, Jr. et al. |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095206 A1 | 7/2002 | Addonizio et al. |
| 2002/0100484 A1 | 8/2002 | Hall et al. |
| 2002/0111669 A1 | 8/2002 | Pazienza et al. |
| 2002/0111672 A1 | 8/2002 | Kim et al. |
| 2002/0116044 A1 | 8/2002 | Cottone, Jr. et al. |
| 2002/0123698 A1 | 9/2002 | Garibotto et al. |
| 2002/0138087 A1 | 9/2002 | Shennib et al. |
| 2002/0143285 A1 | 10/2002 | Eno et al. |
| 2002/0143289 A1 | 10/2002 | Ellis et al. |
| 2002/0144696 A1 | 10/2002 | Sharkawy et al. |
| 2002/0161383 A1 | 10/2002 | Akin et al. |
| 2002/0161424 A1 | 10/2002 | Rapacki et al. |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0015816 A1 | 1/2003 | Rapacki et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0073973 A1 | 4/2003 | Evans et al. |
| 2003/0078561 A1 | 4/2003 | Gambale et al. |
| 2003/0100920 A1 | 5/2003 | Akin et al. |
| 2003/0105514 A1 | 6/2003 | Phelps et al. |
| 2003/0120195 A1 | 6/2003 | Milo et al. |
| 2003/0149474 A1 | 8/2003 | Becker |
| 2003/0158573 A1 | 8/2003 | Gittings et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0212413 A1 | 11/2003 | Wilk |
| 2003/0216678 A1 | 11/2003 | March et al. |
| 2003/0216679 A1 | 11/2003 | Wolf et al. |
| 2003/0229366 A1 | 12/2003 | Reggie et al. |
| 2003/0236542 A1 | 12/2003 | Makower |
| 2004/0006298 A1 | 1/2004 | Wilk |
| 2004/0015225 A1 | 1/2004 | Kim et al. |
| 2004/0019348 A1 | 1/2004 | Stevens et al. |
| 2004/0044392 A1 | 3/2004 | Von Oepen |
| 2004/0058097 A1 | 3/2004 | Weder |
| 2004/0059280 A1 | 3/2004 | Makower et al. |
| 2004/0073157 A1 | 4/2004 | Knudson et al. |
| 2004/0073238 A1 | 4/2004 | Makower |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0088042 A1 | 5/2004 | Kim et al. |
| 2004/0106931 A1 | 6/2004 | Guiles et al. |
| 2004/0113306 A1 | 6/2004 | Rapacki et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0133154 A1 | 7/2004 | Flaherty et al. |
| 2004/0133225 A1 | 7/2004 | Makower |
| 2004/0147869 A1 | 7/2004 | Wolf et al. |
| 2004/0158143 A1 | 8/2004 | Flaherty et al. |
| 2004/0167444 A1 | 8/2004 | Laroya et al. |
| 2004/0168691 A1 | 9/2004 | Sharkawy et al. |
| 2004/0186507 A1 | 9/2004 | Hall et al. |
| 2004/0186557 A1 | 9/2004 | Gambale et al. |
| 2004/0186587 A1 | 9/2004 | Ahern |
| 2004/0219180 A1 | 11/2004 | Gambale et al. |
| 2004/0220598 A1 | 11/2004 | Bolduc et al. |
| 2004/0225355 A1 | 11/2004 | Stevens |
| 2004/0236418 A1 | 11/2004 | Stevens |
| 2005/0004505 A1 | 1/2005 | Phelps et al. |
| 2005/0004558 A1 | 1/2005 | Gambale et al. |
| 2005/0033220 A1 | 2/2005 | Wilk et al. |

FOREIGN PATENT DOCUMENTS

| | | |
|---|---|---|
| EP | 0 592 410 B1 | 10/1995 |
| EP | 0 732 088 | 9/1996 |
| EP | 0 815 798 | 7/1997 |
| EP | 0 829 239 | 8/1997 |
| EP | 0 792 624 | 9/1997 |
| EP | 0 797 957 | 10/1997 |
| EP | 0 797 958 | 10/1997 |
| EP | 0 799 604 | 10/1997 |
| EP | 0 801 928 | 10/1997 |
| EP | 0 836 834 | 10/1997 |
| EP | 0 824 903 | 2/1998 |
| EP | 0 876 796 | 5/1998 |
| EP | 0 853 921 | 7/1998 |
| EP | 0 858 779 | 8/1998 |
| EP | 0 876 803 | 11/1998 |
| EP | 0 888 750 | 1/1999 |
| EP | 0 895 752 | 2/1999 |
| EP | 0 903 123 | 3/1999 |
| EP | 0 904 745 | 3/1999 |
| EP | 0 934 728 | 8/1999 |
| EP | 0 955 017 | 11/1999 |
| EP | 0 955 019 | 11/1999 |
| EP | 0 962 194 | 12/1999 |
| EP | 1 020 166 | 7/2000 |
| EP | 1 027 870 | 8/2000 |
| EP | 1 088 564 | 4/2001 |
| EP | 1 097 676 | 5/2001 |
| EP | 1 166 721 | 1/2002 |
| EP | 0 959 815 | 12/2002 |
| EP | 1 112 097 | 6/2003 |
| EP | 0 954 248 B1 | 9/2004 |
| EP | 1 115 452 B1 | 11/2004 |
| EP | 1 477 202 A2 | 11/2004 |
| EP | 1 107 710 B1 | 12/2004 |
| EP | 1 484 081 A1 | 12/2004 |
| EP | 1 516 599 A2 | 3/2005 |
| GB | 2 316 322 | 2/1998 |
| JP | 4-505866 | 10/1992 |
| WO | 98/46119 | 10/1988 |
| WO | WO 90/14804 | 12/1990 |
| WO | WO 94/16629 | 8/1994 |

| | | |
|---|---|---|
| WO | WO 96/32972 | 10/1996 |
| WO | WO 96/35469 | 11/1996 |
| WO | WO 96/39962 | 12/1996 |
| WO | WO 96/39964 | 12/1996 |
| WO | WO 96/39965 | 12/1996 |
| WO | WO 96/39965 A1 | 12/1996 |
| WO | 97/13463 | 4/1997 |
| WO | 97/13471 | 4/1997 |
| WO | WO 97/18768 | 5/1997 |
| WO | 97/27893 | 8/1997 |
| WO | 97/27897 | 8/1997 |
| WO | 97/27898 | 8/1997 |
| WO | 97/32551 | 9/1997 |
| WO | WO 97/41916 | 11/1997 |
| WO | WO 97/43961 | 11/1997 |
| WO | WO 98/02099 | 1/1998 |
| WO | WO 98/03118 | 1/1998 |
| WO | 98/06356 | 2/1998 |
| WO | 98/08456 | 3/1998 |
| WO | 98/10714 | 3/1998 |
| WO | 98/16161 | 4/1998 |
| WO | WO 98/19607 | 5/1998 |
| WO | WO 98/19625 | 5/1998 |
| WO | 98/25549 | 6/1998 |
| WO | WO 98/24373 | 6/1998 |
| WO | WO 98/25533 | 6/1998 |
| WO | WO 98/38916 | 9/1998 |
| WO | WO 98/38925 | 9/1998 |
| WO | WO 98/38939 | 9/1998 |
| WO | WO 98/38941 | 9/1998 |
| WO | WO 98/39038 | 9/1998 |
| WO | 98/46115 | 10/1998 |
| WO | WO 98/44869 | 10/1998 |
| WO | WO 98/49964 | 11/1998 |
| WO | WO 98/53759 | 12/1998 |
| WO | WO 98/55027 | 12/1998 |
| WO | WO 98/57590 | 12/1998 |
| WO | WO 98/57591 | 12/1998 |
| WO | WO 98/57592 | 12/1998 |
| WO | 99/08624 | 2/1999 |
| WO | WO 99/07296 | 2/1999 |
| WO | 99/17683 | 4/1999 |
| WO | WO 99/15220 | 4/1999 |
| WO | WO 99/17671 | 4/1999 |
| WO | 99/21490 | 5/1999 |
| WO | 99/25273 | 5/1999 |
| WO | WO 99/21510 | 5/1999 |
| WO | WO 99/22655 | 5/1999 |
| WO | WO 99/22658 | 5/1999 |
| WO | WO 99/27985 | 6/1999 |
| WO | 99/36000 | 7/1999 |
| WO | 99/36001 | 7/1999 |
| WO | WO 99/32051 | 7/1999 |
| WO | WO 99/35977 | 7/1999 |
| WO | WO 99/35979 | 7/1999 |
| WO | WO 99/35980 | 7/1999 |
| WO | WO 99/37218 | 7/1999 |
| WO | 99/38459 | 8/1999 |
| WO | 99/40868 | 8/1999 |
| WO | WO 99/40853 | 8/1999 |
| WO | WO 99/40963 | 8/1999 |
| WO | 99/48545 | 9/1999 |
| WO | WO 99/44524 | 9/1999 |
| WO | WO 99/47071 | 9/1999 |
| WO | WO 99/47078 | 9/1999 |
| WO | WO 99/48427 | 9/1999 |
| WO | WO 99/48549 | 9/1999 |
| WO | 99/49793 | 10/1999 |
| WO | 99/49910 | 10/1999 |
| WO | 99/51162 | 10/1999 |
| WO | 99/53863 | 10/1999 |
| WO | WO 99/49910 A2 | 10/1999 |
| WO | WO 99/55406 | 11/1999 |
| WO | 99/60941 | 12/1999 |
| WO | 99/62430 | 12/1999 |
| WO | 00/09195 | 2/2000 |
| WO | WO 00/09195 A1 | 2/2000 |
| WO | 00/12029 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/15275 | 3/2000 |
| WO | WO 00/10623 | 3/2000 |
| WO | WO 00/13722 | 3/2000 |
| WO | WO 00/16848 A1 | 3/2000 |
| WO | 00/21436 | 4/2000 |
| WO | 00/21461 | 4/2000 |
| WO | 00/21463 | 4/2000 |
| WO | WO 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | 00/24449 | 5/2000 |
| WO | 00/33725 | 6/2000 |
| WO | WO 00/35376 | 6/2000 |
| WO | WO 00/36997 | 6/2000 |
| WO | 00/41632 | 7/2000 |
| WO | 00/41633 | 7/2000 |
| WO | WO 00/43051 | 7/2000 |
| WO | 00/45711 | 8/2000 |
| WO | 00/48530 | 8/2000 |
| WO | WO 00/45886 | 8/2000 |
| WO | WO 00/49952 | 8/2000 |
| WO | WO 00/49954 | 8/2000 |
| WO | WO 00/49956 | 8/2000 |
| WO | 00/56387 | 9/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | WO 00/56387 | 9/2000 |
| WO | 00/66007 | 11/2000 |
| WO | 00/66009 | 11/2000 |
| WO | 00/66035 | 11/2000 |
| WO | 00/71195 | 11/2000 |
| WO | WO 00/69345 | 11/2000 |
| WO | WO 00/69504 | 11/2000 |
| WO | 01/10340 | 2/2001 |
| WO | 01/10341 | 2/2001 |
| WO | 01/10347 | 2/2001 |
| WO | 01/10348 | 2/2001 |
| WO | 01/10349 | 2/2001 |
| WO | WO 01/08566 | 2/2001 |
| WO | WO 01/08602 | 2/2001 |
| WO | WO 01/10350 A1 | 2/2001 |
| WO | WO 01/17440 A1 | 3/2001 |
| WO | WO 01/26562 | 4/2001 |
| WO | WO 01/49187 A1 | 7/2001 |
| WO | WO 01/54625 | 8/2001 |
| WO | WO 01/70133 | 9/2001 |
| WO | WO 02/02163 | 1/2002 |
| WO | WO 02/02168 | 1/2002 |

OTHER PUBLICATIONS

Alfred Goldman, Seymour M. Greenstone, Fred S. Preuss, Sherman H. Strauss & En-Shu Chang; "Experimental Methods for Producing a Collateral Circulation to the Heart Directly from the Left Ventricle"; Journal of Thoracic Surgery; Mar. 1956; pp. 364-374; vol. 31, No. 3; U.S.A.

Frank M. Galioto, Milton J. Reitman, Arnold J. Slovis & Irving A. Sarot; "Right coronary artery to left ventricle fistula: A case report and discussion"; American Heart Journal; Jul. 1971; pp. 93-97; vol. 82, No. 1; The C.V. Mosby Company; St. Louis, MO.

Joseph P. Archie Jr.; "Intramyocardial Pressure: Effect of Preload on Transmural Distribution of Systolic Coronary Blood Flow"; The American Journal of Cardiology; Jun. 1975; pp. 904-911; vol. 35; U.S.A.

L. Levinsky, T.Z. Lajos, A.B. Lee, Jr., C. Espersen, & G. Schimert; "The Revival of the Horseshoe Graft (Side-toSide Saphenous-Vein-to-Aorta Anastomosis"; The Thoracic and Cardiovascular Surgeon; Oct. 1979; pp. 322-324; vol. 27, No. 5; Georg Thieme Publishers; Stuttgart, Germany.

S. Sultan Ahmed, Bunyad Haider & Timothy J. Regan; "Silent left coronary artery-cameral fistula: probable cause of myocardial ischemia"; American Heart Journal; Oct. 1982; pp. 869-870; vol. 104, No. 4, pt. 1; The C.V. Mosby Company; St. Louis, MO.

Goetz M. Richter, Gerd Noeldge, Julio C. Palmaz, Martin Roessle, Volker Slegerstetter, Martina Franke, Wolfgang Gerok, Werner Wenz & Edward Farthman; "Transjugular Intrahepatic Portacaval Stent Shunt: Preliminary Clinical Results"; Radiology; Mar. 1990; pp. 1027-1030; vol. 174, No. 3, Pt. 2; The Radiological Society of North America; Oak Brook, IL.

Medical Industry Today Headline News; "Eclipse Gets OK to Pump Catheter Marketing in Europe"; Ju. 17, 1998; pp. 1-2; Article #07179802, Article is 349 words long; Medical Data International, Inc.; Santa Ana, CA.

Medical Industry Today Headline News; "Sales Dive, Losses Soar in 2Q for CardioGenesis"; Jul. 17, 1998; pp. 1-2; Article #07179808, Article is 560 words long; Medical Data International, Inc.; U.S.A.

Howard A. Cohen & Marco Zenati; "Alternative Approaches to Coronary Revascularization"; Current International Cardiology Reports; 1999; pp. 138-146; vol. 1; Current Science, Inc.; U.S.A.

Stephen N. Oesterle, Nicolaus Reifart, Motoya Hayase, Eugen Haputmann, Reginald Low, Raimund Erbel, Michael Hause, Olaf Dirsch, Gerhard C. Schuler, Renu Virmani & Alan C. Yeung; "Catheter-Based Coronary Bypass: A Development Update"; Catheterization and Cardiovascular Interventions; 2003; pp. 212.218; vol. 58; Wiley-Liss, Inc.; U.S.A.

Banning G. Lary & Roger W. Sherman; "A method for creating a coronary-myocardial artery"; Surgery; Jun. 1966; pp. 1061-1064; vol. 59, No. 6; The C.V. Mosby Company; St. Louis, MO.

Zemel, M.D. et al., "Percutaneous Transjugular Portosystemic Shunt," JAMA, 1991, vol. 266, No. 3, pp. 390-393.

Massimo, M.D. et al., "Myocardial Revascularization by a New Method of Carrying Blood Directly from the Left Ventricular Cavity into the Coronary Circulation," Journal of Thoracic Sueons, Aug. 1997, vol. 34, No. 2, pp. 257-264.

Lary, M.D. et al., "Myocardial Revascularization Experiments Using the Epicardium," Archives of Surgery, Jan. 1969, vol. 98, No. 1, pp. 69-72.

Munro, M.D. et al., "The possibility of myocardial revascularization by creation of a left ventriculocoronary artery fistula," Journal of Thoracic and Cardiovascular Surgery, Jul. 1969, vol. 58, No. 1, pp. 25-32.

Kuzela, M.D. et al., "Experimental evaluation to direct transventricular revascularization," The Journal of Thoracic and Cardiovascular Surgery, Jun. 1969, vol. 57, No. 6, pp. 770-773.

American Medical Association Publication; International Cardiovascular Society, "Myocardial Boring for the Ischemic Heart," A. Wakabayashi, M.D., et al.; Fifteenth Scientific Meeting, Atlantic City, NJ, Jun. 16 and 17, 1967; Archives of Surgery, pp. 743-752, vol. 95, No. 5, Nov. 1967.

The Journal of Thoracic and Cardiovascular Surgery, "Experimental evaluation of myocardial tunnelization as a method of myocardial revascularization," I. Anabtawi, M.D. et al., pp. 638-646, Nov. 1969.

American Heart Journal, "Effects of laser irradiation delivered by flexible fiberoptic system on the left ventricular internal myocardium," G. Lee, M.D. et al., pp. 587-590, vol. 106, No. 3, Sep. 1983.

Texas Heart Institute Journal, "Transmyocardial Laser Revascularization," D. A. Cooley, M.D. et al., pp. 220-224, vol. 21, No. 3, 1994.

American Journal of Physiology, "Transmural myocardial perfusion during restricted coronary inflow in the awake dog," R. Bache et al., pp. H645-651, vol. 232, No. 6, Jun. 1977.

The Annals of Thoracic Surgery, "Myocardial Canalization, " A. H. Khazei, M.D. et al., vol. 6, No. 2, Aug. 1968.

Surgical Forum, "Proceedings of the 24th Annual Sessions of the Forum on Fundamental Surgical Problems, 54th Clinical Congress of the American College of Surgeons, Chicago, Illinois, Oct., 1968," pp. 156-159, American College of Surgeons, Chicago, Illinois.

Tweden et al., "Ventriculocoronary Artery Bypass (VCAB), a Novel Approach to Myocardial Revascularization" Feb. 2000.

Gardner, M.D. et al., "An Experimental Anatomic Study of Indirect Myocardial Revascularization," Journal of Surgical Research, May 1971, vol. 11, No. 5, pp 243-247.

Palmaz et al., "Expandable Intrahepatic Portacaval Shunt Stents: Early Experience in the Dog," AJR, 1985, vol. 145, pp. 821-825.

Palmaz et al., "Expandable Intrahepatic Portacaval Shunt Stents in Dogs with Chronic Portal Hypertension," AJR, 1986, vol. 147, pp. 1251-1254.

Richter, M.D. et al., "Transjugular Intrahepatic Portacaval Stent Shunt: Preliminary Clinical Results," Radiology, 1990, vol. 174, No. 3, pp. 1027-1030.

US 6,331,185, 12/2001, Gambale et al. (withdrawn)

* cited by examiner

VALVE DESIGNS FOR LEFT VENTRICULAR CONDUITS

CROSS-REFERENCE TO RELATED APPLICATION

This application claims the benefit of U.S. Provisional Application Ser. No. 60/099,777, filed Sep. 10, 1998.

FIELD OF THE INVENTION

This invention relates to apparatus and method for implanting a conduit to allow communication of fluids from one portion of a patient's body to another; and, more particularly, to a blood flow conduit to allow communication from a heart chamber to a vessel or vice versa, and/or vessel to vessel. Even more particularly, the invention relates to a left ventricular conduit and related conduit configurations for controlling the flow of blood through the conduit to achieve bypass of a stenosed or occluded coronary artery.

BACKGROUND OF THE INVENTION

Coronary artery disease is a major problem in the U.S. and throughout the world. Coronary arteries as well as other blood vessels frequently become clogged with plaque, which at the very least impairs the efficiency of the heart's pumping action, and can lead to heart attack, arrhythmias, and death. In some cases, these arteries can be unblocked through noninvasive techniques such as balloon angioplasty. In more difficult cases, a bypass of the blocked vessel is necessary.

In a bypass operation, one or more venous segments are inserted between the aorta and the coronary artery. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass surgery, however, is a very intrusive procedure that is expensive, time-consuming and traumatic to the patient. The operation requires an incision through the patient's sternum (sternotomy), and that the patient be placed on a bypass pump so that the heart can be operated on while not beating. A vein graft is harvested from the patient's leg, and a delicate surgical procedure is required to piece the bypass graft to the coronary artery (anastomosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type of location of the blockage or stenosis, or due to the risk of emboli.

Thus, there is a need for an improved bypass system that is less traumatic to the patient.

SUMMARY OF THE INVENTION

The preferred embodiments of the present invention address the need in the previous technology by providing a bypass system that avoids the sternotomy and other intrusive procedures normally associated with coronary bypass surgery. These embodiments also free the surgeon from the need to perform multiple anastomoses as is necessary in the current process.

The preferred device provides a conduit or shunt for diverting blood directly from the left ventricle of the heart to a coronary artery, at a point distal to the blockage or stenosis, thereby bypassing the blocked portion of the vessel. The conduit preferably comprises a tube adapted to be positioned in the myocardium and having a one way valve therein. The valve prevents the backflow of blood from the coronary artery into the left ventricle.

The conduit device is delivered through the coronary artery to a position distal the blockage or stenosis. At that position, the coronary artery, the myocardium and the wall of the left ventricle are pierced to provide an opening or channel completely through from the coronary artery to the left ventricle of the heart. The conduit is then positioned in the opening to provide a permanent passage for blood to flow between the left ventricle of the heart and the coronary artery, distal to the blockage or stenosis. The conduit is sized so that one open end is positioned within the coronary artery, while the other open end is positioned in the left ventricle. The hollow lumen of the conduit provides a passage for the flow of blood.

To prevent the backflow of blood from the coronary artery to the left ventricle of the heart, the conduit is provided with a one-way valve. The valve is preferably a windsock type valve, a flapper valve, a bi- or tricuspid valve, a ball valve, a valve formed from the myocardium itself, or a valve that opens and closes in response to the contraction and relaxation of the heart muscle, or in response to the electrical signals in the heart.

DETAILED DESCRIPTION OF THE PREFERRED EMBODIMENT

Figure 1A:
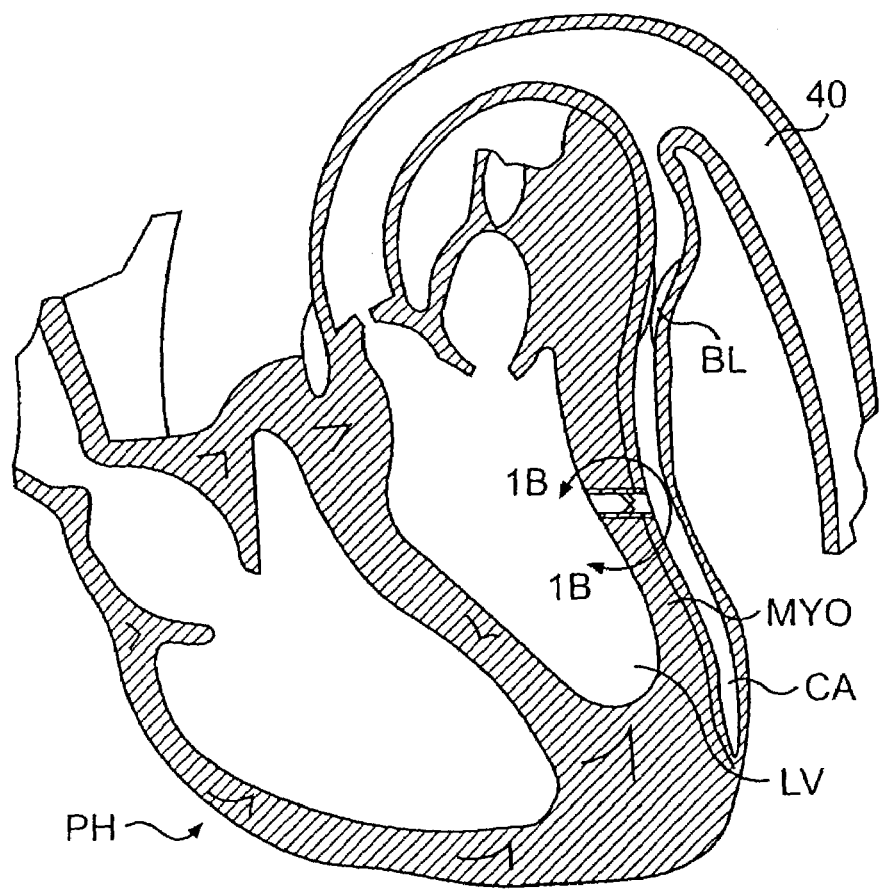
FIG. 1A is a schematic, cross-sectional view of a human heart, showing a conduit in the myocardium of the heart for forming a bypass between the left ventricle and a coronary artery.

As is well known, the coronary artery branches off the aorta and is positioned along the external surface of the heart wall. Oxygenated blood that has returned from the lungs to the heart then flows from the heart to the aorta. Some blood in the aorta flows into the coronary arteries, and the remainder of blood in the aorta flows on to the remainder of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

As used herein, the term "heart chamber" primarily refers to the interior, or lumenal, aspect of the left or right ventricle or the left or right atrium. The term "conduit," "stent," and "tube" herein refer to physical structures, preferably primarily artificial, that can be positioned between two or more chambers or vessels, to allow blood flow from one chamber or vessel to another. A "shunt" is any natural or artificial passage between natural channels, such as heart chambers or blood vessels. The conduit in the preferred arrangement can be made of a variety of materials, including various metals, such as nitinol, or plastics.

As used herein, the term "heart wall" comprises any one or more of the following portions or layers of the mammalian heart: the epicardium, myocardium, endocardium, pericardium, interatrial septum, and interventricular septum.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even noncardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the obstructions that are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods are disclosed. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In order to restore the flow of oxygenated blood through the coronary artery, the preferred arrangement provides for the shunting of blood directly from the heart to a site in the coronary artery which is distal the blockage or stenosis.

Although the specification herein will describe the conduit primarily with reference to the left ventricle, the preferred arrangement can be used with any of the four heart chambers, and with any coronary artery, including the left main coronary artery, the right coronary artery, the left anterior descending artery, the left circumflex artery, the posterior descending artery, the obtuse marginal branch or a diagonal branch.

A tunnel or opening is formed through the wall of the coronary artery and the heart wall and into the left ventricle of the heart which lies beneath, or deep to, the coronary artery. A conduit is positioned in the opening to keep it open, and a one-way valve is positioned within the conduit to prevent blood from flowing back into the left ventricle of the heart from the coronary artery.

The conduit may be introduced into the heart wall in a variety of ways, including by a catheter threaded through the femoral artery into the aorta and thence into the left ventricle and, if necessary, the left atrium; or by a catheter threaded through the femoral vein into the inferior vena cava and thence into the night atrium and right ventricle. Alternatively, the conduit may be introduced through a surgical incision in chest wall (thoracotomy) or sternum (sternotomy).

Further details regarding conduits and conduit delivery systems are described in U.S. patent applications entitled DELIVERY METHODS FOR LEFT VENTRICULAR CONDUIT U.S. application Ser. No. 09/368,868, now U.S. Pat. No. 6,261,304; DESIGNS FOR LEFT VENTRICULAR CONDUIT U.S. application Ser. No. 09/369,048, now U.S. Pat. No. 6,290,728; LEFT VENTRICULAR CONDUIT WITH BLOOD VESSEL GRAFT U.S. application Ser. No. 09/369,061, now U.S. Pat. No. 6,254,564; LEFT VENTRICULAR CONDUITS TO CORONARY ARTERIES AND METHODS FOR CORONARY BYPASS U.S. application Ser. No. 90/369,039, now abandoned, and BLOOD FLOW CONDUIT DELIVERY SYSTEM AND METHOD OF USE U.S. application Ser. No. 09/368,644, now U.S. Pat. No. 6,302,892, filed on the same day as the present application, and U.S. Pat. Nos. 5,429,144 and 5,662,124, the disclosures of which are all hereby incorporated by reference in their entirety.

The opening through the heart wall (including endocardium, myocardium, and epicardium) and coronary artery can be formed in a variety of ways, including by knife or scalpel, electrocautery, cryoablation, radiofrequency ablation, ultrasonic ablation, and the like. Other methods will be apparent to those of ordinary skill in the art.

Figure 1B:
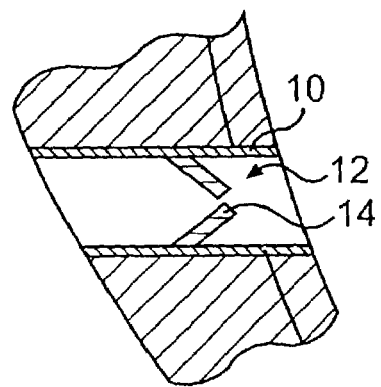
FIG. 1B is an enlarged view of the bypass conduit of FIG. 1A.

Referring now to FIGS. 1A and 1B, a coronary artery bypass is accomplished by disposing a conduit 12 (FIG. 1B) in a heart wall or myocardium MYO of a patient's heart PH (FIG. 1A). The conduit 12 preferably extends from the left ventricle LV of heart PH to a clogged coronary artery CA at a point downstream of a blockage BL to create a passageway therethrough. Conduit 12 is preferably made of a biocompatible material such as stainless steel or nitinol, although other materials such as Ti, Ti alloys, Ni alloys, Co alloys and biocompatible polymers may also be used. In one embodiment, conduit 12 has a one way valve 14 to allow blood to flow from the left ventricle LV to the coronary artery CA. Although the conduit 12 may elastically deform under the contractive pressure of the heart muscle during systole, the stent remains open to allow blood to pass from the patient's left ventricle LV into the coronary artery CA. During diastole, the blood pumped into coronary artery through passageway is blocked by one-way valve 14 from returning to left ventricle LV.

Figure 2:
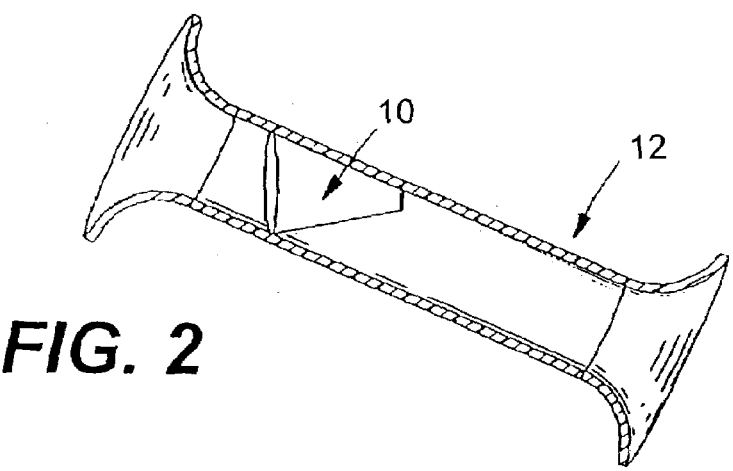
FIG. 2 is a cross-sectional view of a windsock valve incorporated into a heart conduit in accordance with a preferred arrangement.

One embodiment of the preferred arrangement is illustrated in FIG. 2. The valve 10 incorporates a design similar to a windsock. The valve 10 is preferably formed from a biocompatible fabric-like material incorporated during the construction of the conduit 12. The high-pressure blood flow causes the valve 10 to open, while the backflow of blood catches the edges of the valve 10 and causes it to close, stopping the flow. The valve 10 can be positioned anywhere along the length of the conduit 12.

The valve 10 is preferably constructed from a biocompatible and very compliant fabric or other material that is pushed aside by the high forward blood pressure created from the contraction of the heart muscle, but opens to "catch" the back-flow of blood passing back through the conduit 12. The valve 10 is preferably constructed by incorporating the fabric or other material into the conduit 12 directly during its manufacture. This allows the valve 10 and conduit 12 to be introduced as a single unit.

Figure 3:
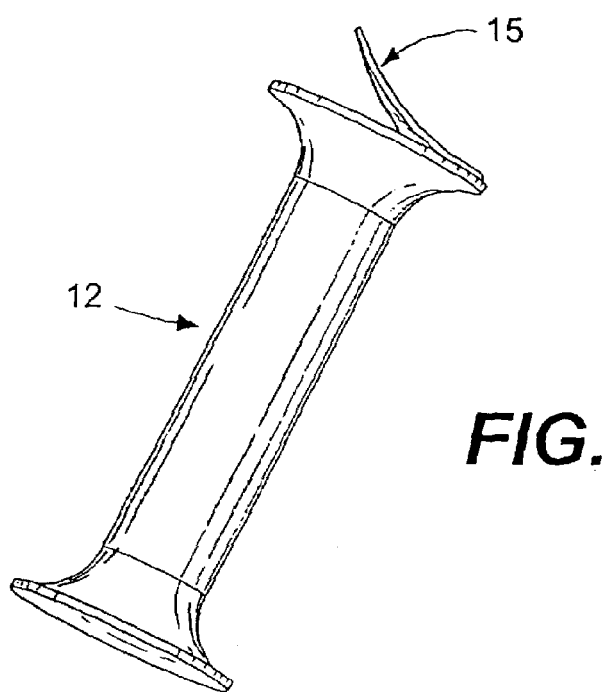
FIG. 3 is a perspective view of a flapper valve incorporated into a heart conduit in accordance with a preferred arrangement.

Another embodiment of the preferred arrangement is illustrated in FIG. 3. This valve 15 is a type of "flapper valve" that is built onto the end of the conduit 12 that is positioned in the coronary artery. The high-pressure blood flow opens the flap 15 and the backflow of blood causes the flap 15 to shut. This flap 15 is slightly larger than the conduit 12 inner diameter (ID) to accomplish this action and to ensure a proper seal. The valve 15 is preferably formed from the same material as the conduit 12 and the two are preferably introduced as a single unit. Alternatively, the valve 15 may be attached as a secondary operation once the conduit 12 is in place.

Figure 4:
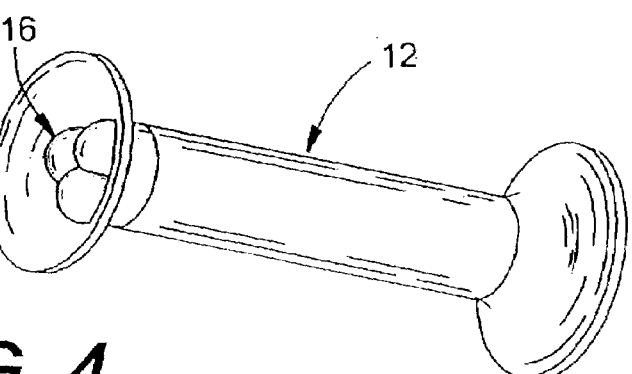
FIG. 4 is a perspective view of a tricuspid valve incorporated into a heart conduit in accordance with the preferred arrangement.

The third embodiment of the valve 16 is illustrated in FIG. 4. This valve 16 is similar to a natural heart valve. A bi- or tricuspid arrangement of semi-circular spheres is forced open by the high-pressure flow and collapses back to prevent backflow of blood through the conduit 12. This valve 16 is preferably made from the same material as the conduit 12, or alternatively, from a thin biocompatible material that is built onto the conduit 12. Preferably, the valve 16 and the conduit 12 are manufactured together and introduced as a single unit. Alternatively, the valve 16 may be attached to the conduit 12 in a secondary operation once the conduit 12 is in place. The valve 16 may be placed at any location along the length of the conduit 12.

Figure 5A:
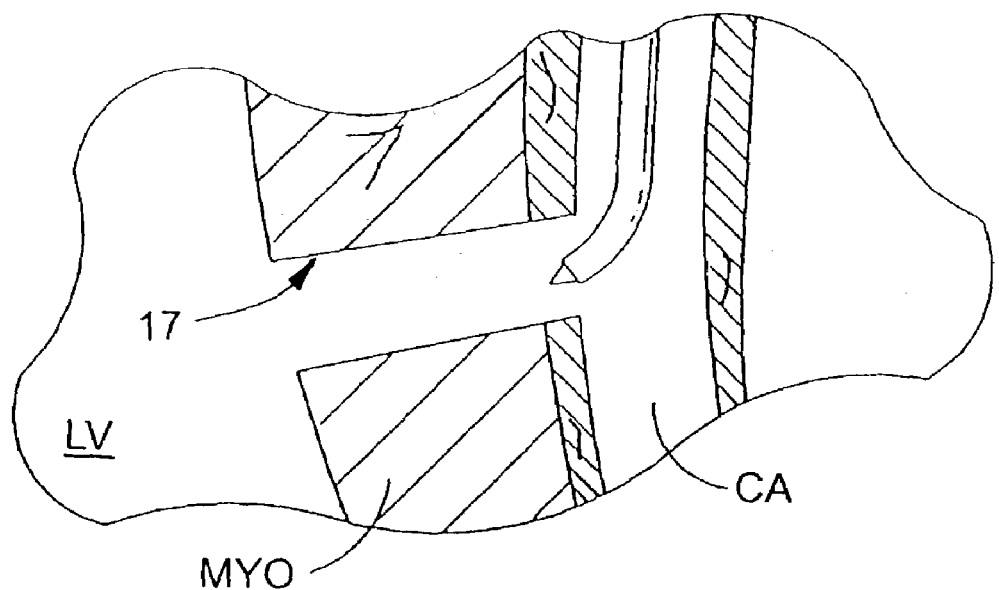
FIGS. 5A–D are cross-sectional views of a valve formed from the myocardium for use in conjunction with a heart conduit in accordance with a preferred arrangement.
Figure 5B:
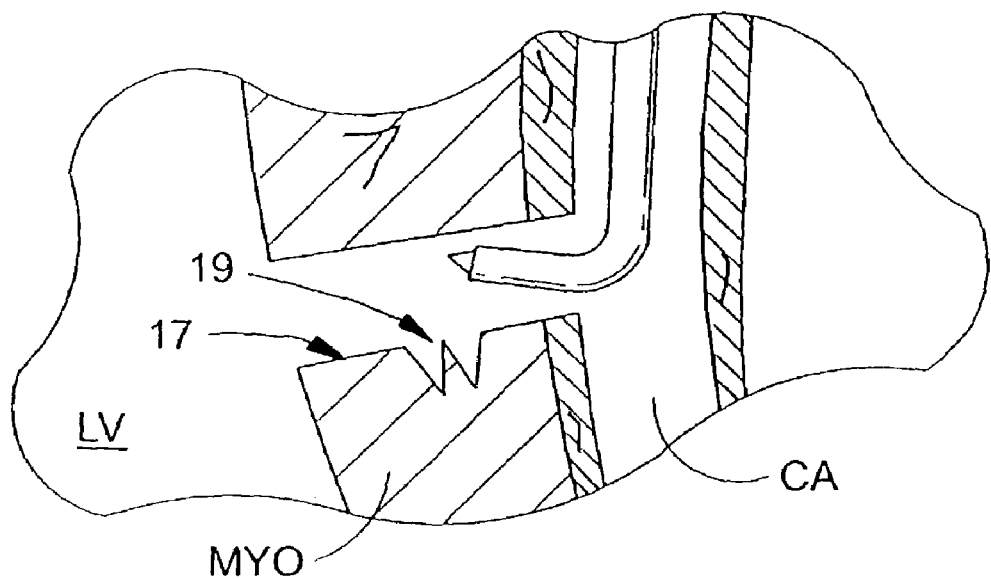

A further embodiment of the conduit is illustrated in FIGS. 5A–D. Here, the heart wall, which includes the myocardium MYO, lying between the coronary artery CA and the left ventricle of the heart LV, is cut using known techniques to form a passage through the myocardium MYO. FIG. 5A shows the myocardium MYO after a cut or puncture has been made in it, with a free edge 17 shown at each margin of the cut or puncture. FIG. 5B shows the myocardium MYO after a jagged or irregular surface 19 has been made with a cutting tool in the free edge 17 of the myocardium MYO. Such cutting tools may include knives, scalpels, lasers, radiofrequency probes, and other cutting tools known to those of skill in the art.

Figure 5C:
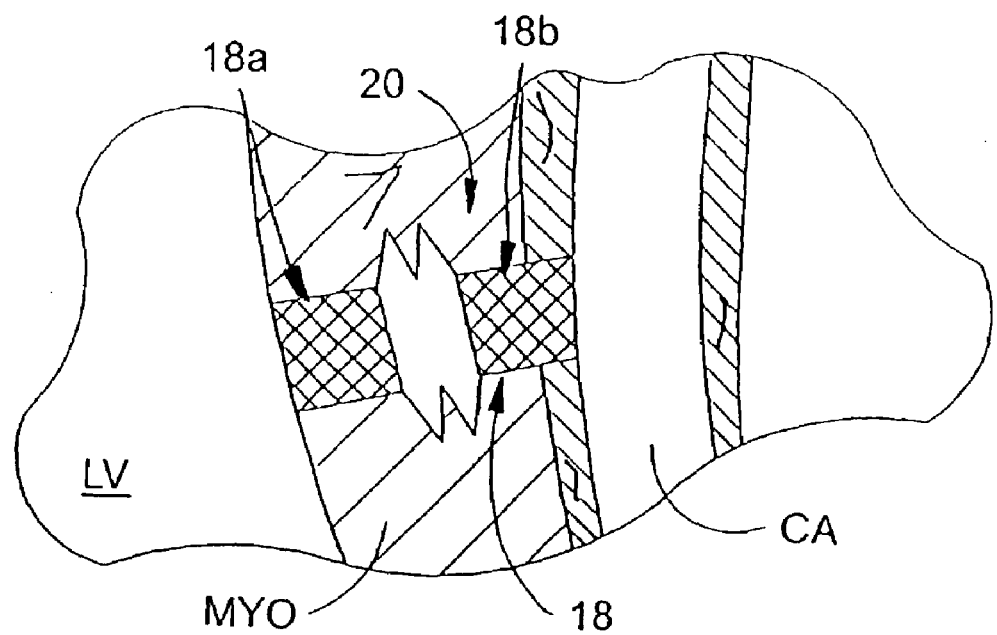
Figure 5D:
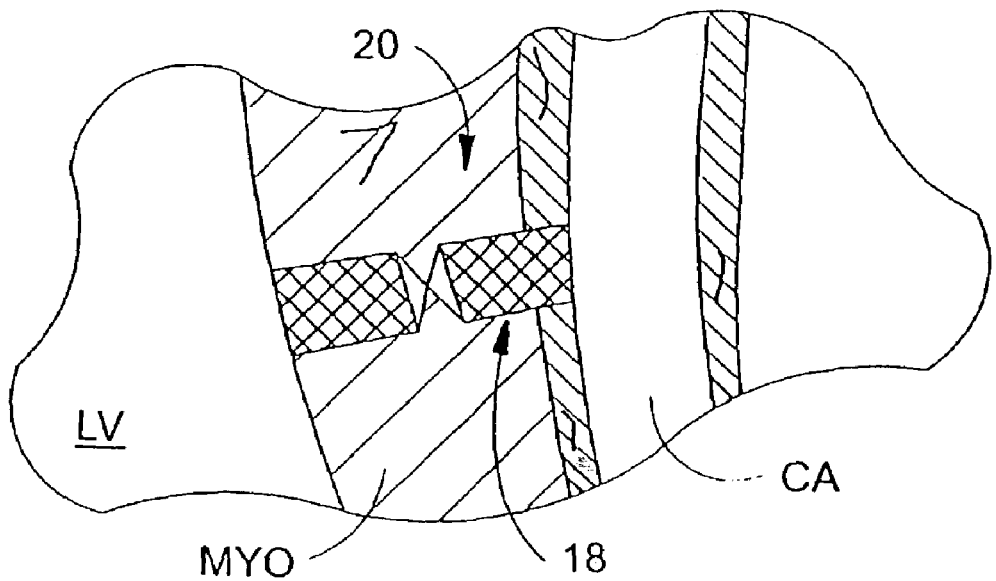

As illustrated in FIG. 5C, two conduits, an upper or lower conduit, or a single conduit 18 having upper 18a and lower 18b components, is positioned in the passage. The myocardium MYO is left free between the two edges of the conduit 18 to form the valve 20. FIG. 5D shows that during diastole, the edges or free portions of the myocardium MYO come together, closing the passage through the myocardium MYO. During systole, the free portions of the myocardium MYO can move away from one another as cardiac myofibrils contract, opening the passage through the myocardium MYO, as illustrated in FIG. 5C. Thus, the heart muscle MYO itself can form at least part of the valve 20 in the conduit 18 to prevent the backflow of blood.

Figure 6A:
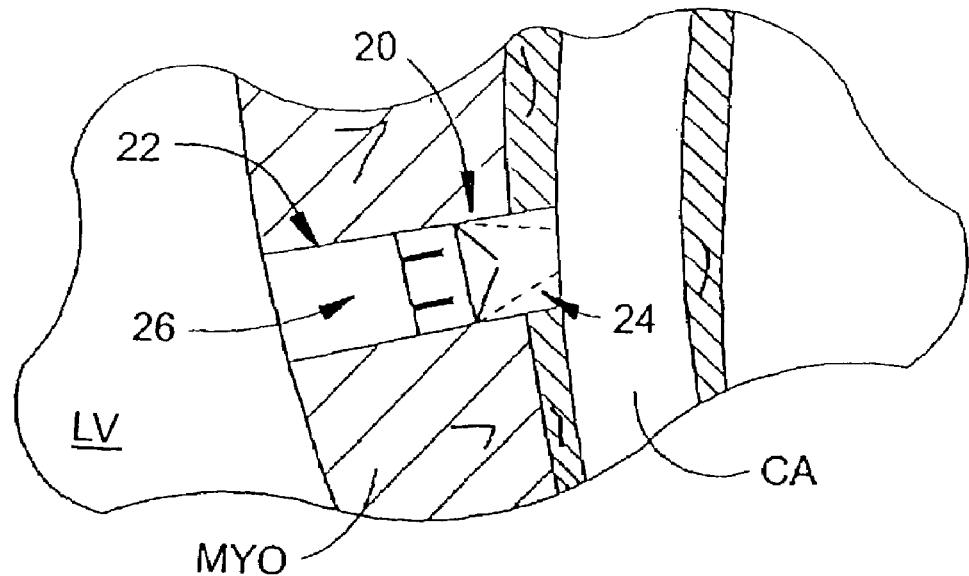
FIGS. 6A–B are cross-sectional views of a valve that is activated by the contractions of the heart muscle for use in conjunction with a heart conduit in accordance with a preferred arrangement.
Figure 6B:
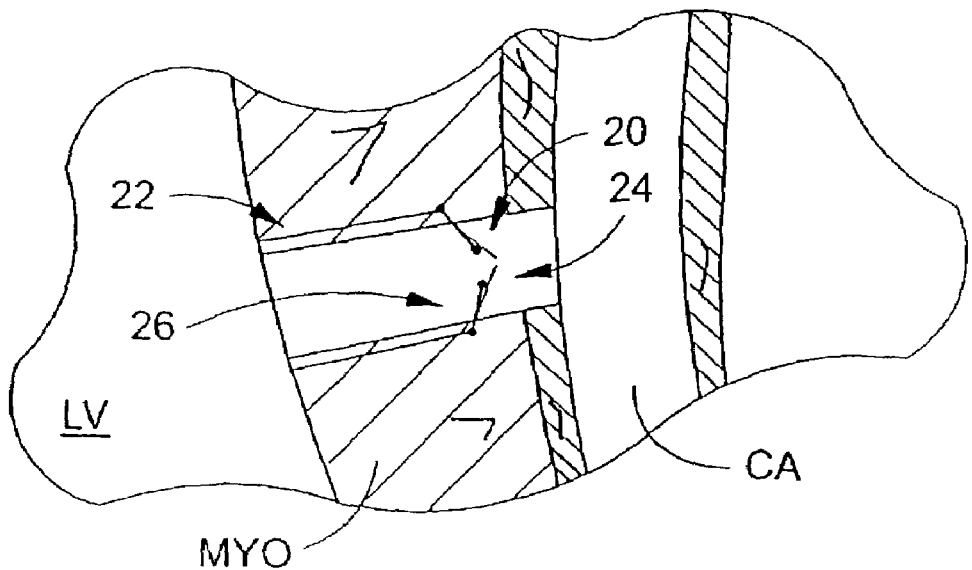

In another embodiment, the valve in the conduit may be controlled in response to the contractions of the heart. As illustrated in FIGS. 6A and 6B, two conduits (FIG. 6A), an upper conduit 20 and lower conduit 22, or a single conduit (FIG. 6B) having upper moveable components 20 and lower moveable components 22, are positioned in the passage in the myocardium MYO between the left ventricle LV and the coronary artery CA. The conduit or conduits contain a valve 24, which is normally in a closed position, and an actuator 26, which is adapted to open the valve 24 in the conduit. During diastole, when the heart muscle MYO is relaxed, the two conduits or the two components of the conduit 20, 22 are positioned such that the valve 24 remains closed. During systole, the two conduits or components 20, 22 are brought close together, such that the actuator 26 forces the valve 24 to open and allows for the passage of blood therethrough. Thus, the contractions of the heart muscle MYO control the valve 24 in the conduit to prevent the backflow of blood during part of the cardiac cycle, for example diastole.

The valve 24 may also be controlled by a hydrodynamic or electric pump or motor, which is responsive to the contractions of the heart, causing the valve 24 to open and close in response to various parts of the cardiac cycle.

Figure 7:
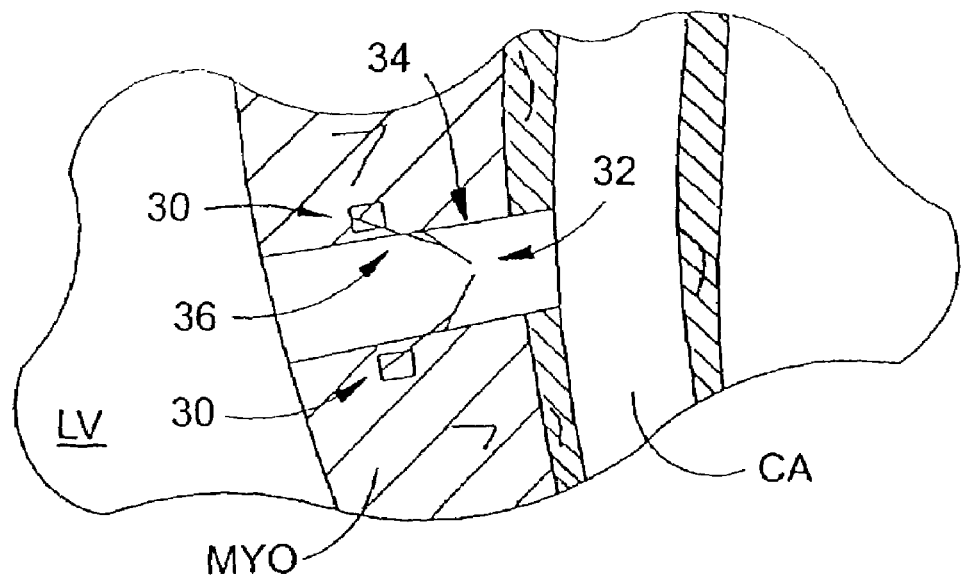
FIG. 7 is a cross-sectional view of a valve that is activated by the electrical signals in the heart muscle for use in conjunction with a heart conduit in accordance with a preferred arrangement.

A further embodiment of the preferred arrangement is illustrated in FIG. 7. In this embodiment, electrical sensors 30 regulate the opening and closing of the valve 32 positioned within the conduit 34. The sensor 30 senses the electrical signals produced in the heart muscle, and causes the valve 32 to open during systole, and to close during diastole. This is accomplished by having an actuator 36 act in response to the electrical signals detected by the sensor 30, to open and close the valve 32. For example, the valve 32 can be biased in a closed position. When the sensor 30 detects the electrical signal that occurs during or immediately precedes systole, e.g., a QRS complex in the electrocardiogram, the sensor 30 signals the actuator 36 to force open the valve 32 and allow for the flow of blood therethrough. During diastole, the sensor 30 signals the actuator 36 to allow the valve 32 to close and prevent any backflow of blood. Alternatively, the valve 32 can be biased in an open position. When the sensor 30 senses diastole, such as through coordination with the P wave or PR interval in the electrocardiogram, or, for example, after the sensor delays for a predetermined time period after the QRS complex occurs in the electrocardiogram, it signals the actuator 36 to close the valve 32 and prevent the backflow of blood.

Figure 8:
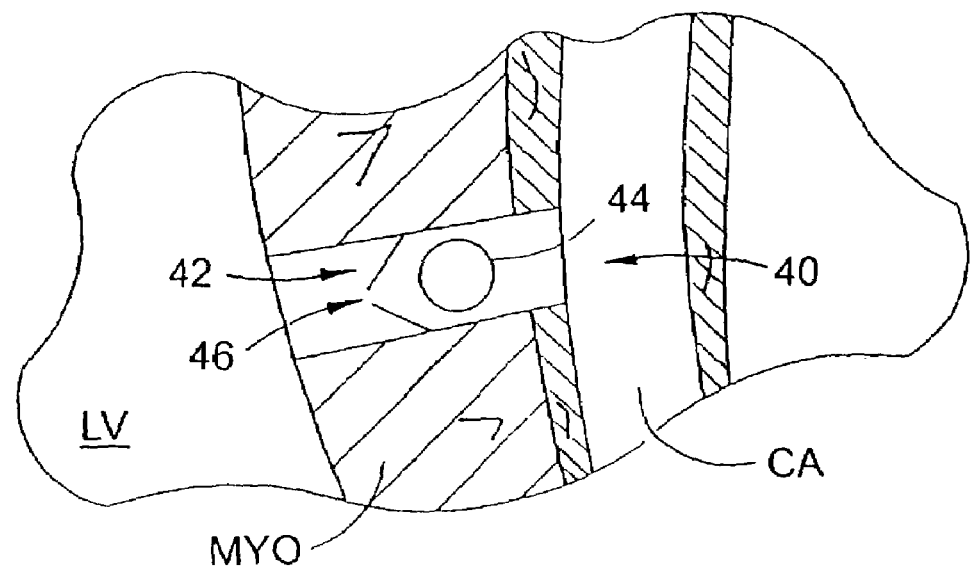
FIG. 8 is a cross-sectional view of a ball valve incorporated into a heart conduit in accordance with a preferred arrangement.

Another embodiment is illustrated in FIG. 8. This valve 42 is a type of "ball valve" that is built into the conduit 40 that is positioned in the coronary artery. The high-pressure blood flow from the left ventricle LV to the coronary artery CA opens the valve 42 by moving the ball 44 away from the opening 46. The backflow of blood from the coronary artery CA to the left ventricle LV causes the ball 44 to seat against the opening 46, thereby closing the valve 42 and preventing the backflow of blood. The valve 42 and the conduit 40 are preferably introduced as a single unit.

Figure 9A:
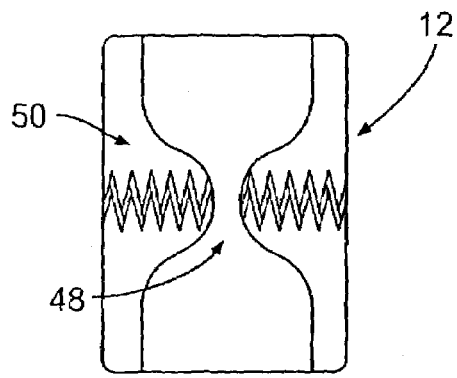
FIG. 9A–9B are cross-sectional views of a valve with spring mechanisms incorporated into a heart conduit.
Figure 9B:
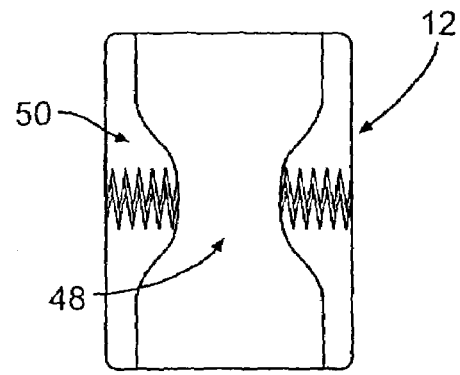

Another embodiment is illustrated in FIGS. 9A and 9B. The conduit 12 has a valve 48 with one or more spring mechanisms 50 within its walls. In diastole (FIG. 9A), bloodflow pressure through the valve is relatively low, and the valve assumes a relatively closed position, impeding the passage of blood through the valve 48. In systole (FIG. 9B), flow pressure through the valve is relatively high, and the valve 48 opens as the spring mechanism 50 contracts, to allow blood to flow through the valve 48.

Figure 9C:
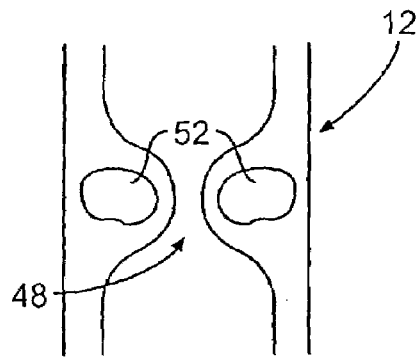
FIGS. 9C–9D are cross-sectional views of a valve with a balloon mechanism incorporated into a heart conduit.
Figure 9D:
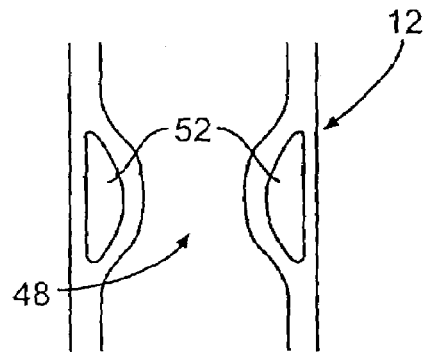
Figure 9E:
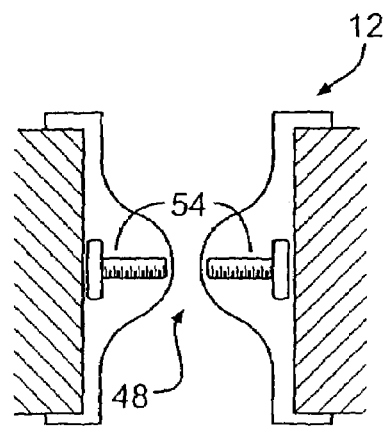
FIGS. 9E–9F are cross-sectional views of a valve with an internal motor incorporated into a heart conduit.
Figure 9F:
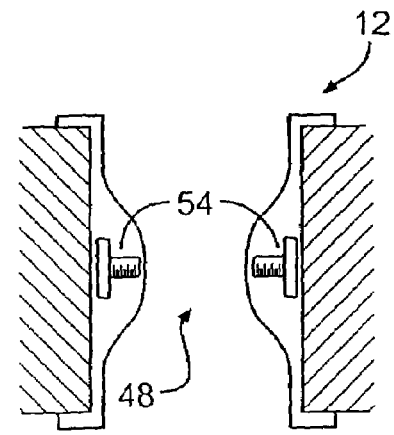

Instead of a spring mechanism 50, the walls of the conduit 12 can have other mechanisms therein to allow differential flow during various parts of the cardiac cycle. For example, the valve 48 can have a gas- or liquid-filled balloon 52 in its wall, as shown in FIGS. 9C and 9D. This balloon mechanism can contract (FIG. 9D, during systole) or expand (FIG. 9C, during diastole) in response to fluid pressure, to allow the valve 48 to open and close, respectively. Alternatively, the valve 48 can have an internal motor 54, shown in FIGS. 9E and 9F, that opens and closes the valve 48 in response to electrical or mechanical signals from the heart during various parts of the cardiac cycle. For example, as illustrated in FIG. 9E, during diastole, the motor preferably closes the valve 48, and during systole, the motor preferably opens the valve 48.

Figure 10A:
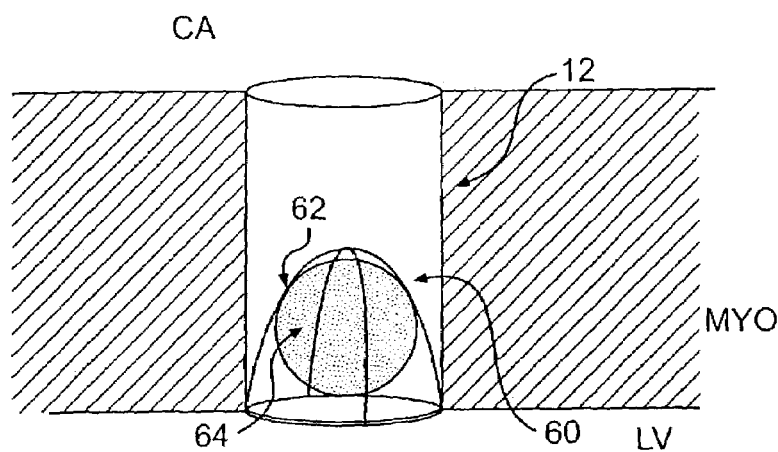
FIG. 10A is a partial cross-sectional view of a ball and cage valve incorporated into a heart conduit.

Another embodiment of the valve mechanism is illustrated in FIG. 10A. The conduit 12 has a ball valve 60 that is of the ball-and-cage variety, for example, like the Starr-Edwards heart valve known to those of skill in the art. This valve 60 typically has a wire or mesh cage 62 with a ball 64 within it. The conduit is positioned within the myocardium MYO. During blood flow from the left ventricle LV to the coronary artery CA, the ball 64 moves toward the apex of the cage 62, permitting blood to flow around the ball 64 and through the conduit 12. During backflow of blood from the coronary artery CA to the left ventricle LV, the ball 64 moves toward the base of the cage 62 and seats thereon, fitting tightly onto the base of the cage 62, and blocking the flow of blood from the coronary artery CA to the left ventricle LV.

Figure 10B:
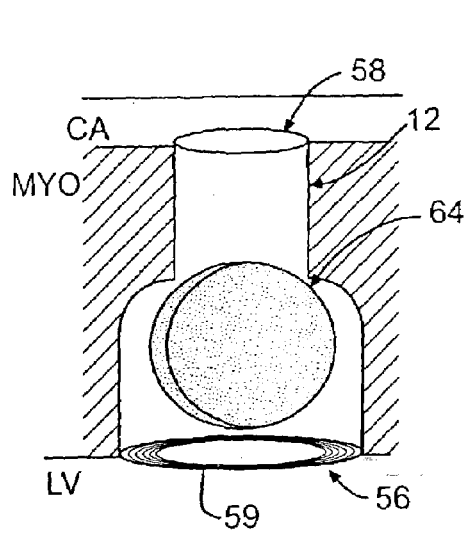
FIG. 10B is a cross-sectional view of a ball valve incorporated into a heart conduit having a narrower distal end.
Figure 10C:
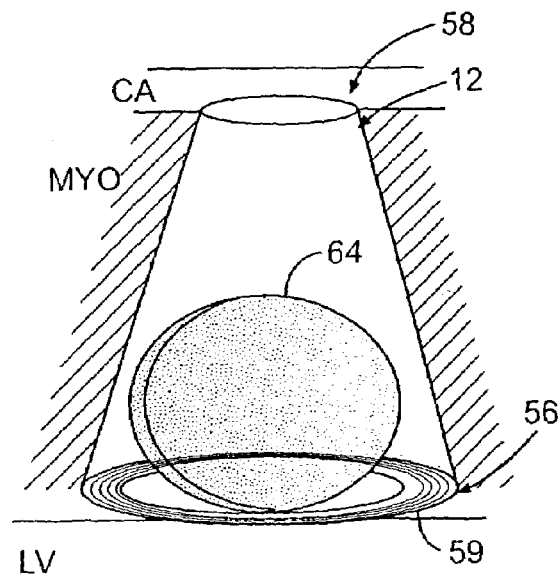
FIG. 10C is a cross-sectional view of a ball valve incorporated into a heart conduit having a smooth taper.

FIG. 10B illustrates another embodiment wherein a ball 64 is provided within a conduit 12 that is wider at proximal end 56 facing the left ventricle, and narrower at distal end 58 facing the coronary artery. FIG. 10C illustrates a similar embodiment wherein the conduit 12 has a gradual taper from the proximal end 56 to distal end 58. Like the embodiment of FIG. 10A, during blood flow from the proximal end 56 to distal end 58, the ball 64 moves toward the coronary artery CA to allow blood flow around the ball through the conduit. In one embodiment, the cross-section of the conduit 12 in FIGS. 10B and 10C is noncircular, for example elliptical, to allow blood to flow around the ball 64. During backflow from the coronary artery CA to the left ventricle LV, the ball moves against the base 59 of the conduit to block flow of blood therethrough.

The present vascular conduit and valve system provides significant improvements in the present treatment of blockages and significant stenoses in the coronary artery. Although the invention has been described in its preferred embodiments in connection with the particular figures, it is not intended that this description should be limited in any way.

What is claimed is:

1. A method of treating a heart, the method comprising:
   providing at least one hollow implant defining a lumen and being configured to be positioned in a heart wall between a heart chamber and a coronary vessel, wherein, when the at least one hollow implant is positioned in the heart wall, the lumen at least partially defines a blood flow passage between the heart chamber and the coronary vessel, and wherein the passage is at least partially closable in response to movement of cardiac tissue during diastole so as to at least partially obstruct blood flow therethrough;
   placing the at least one hollow implant in a heart wall between a heart chamber and a blood vessel; and
   at least partially obstructing blood flow through the at least one hollow implant in response to movement of cardiac tissue during diastole.

2. The method of claim 1, wherein providing the at least one hollow implant includes providing a hollow tube.

3. The method of claim 1, wherein providing the at least one hollow implant wall includes providing a conduit.

4. The method of claim 1, wherein providing the at least one hollow implant includes providing a stent.

5. The method of claim 1, wherein providing the at least one hollow implant heart wall includes providing two hollow implants.

6. The method of claim 5, wherein placing two hollow implants in the heart wall includes placing the hollow implants in the heart wall such that they are separated from each other.

7. The method of claim 6, wherein a length of each of the hollow implants is less than a thickness of the heart wall.

8. The method of claim 1, further comprising permitting blood flow through the at least one hollow implant during systole.

9. The method of claim 1, wherein placing the at least one hollow implant in the heart wall includes placing the at least one hollow implant in the heart wall between a left ventricle and the blood vessel.

10. The method of claim 1, wherein placing the at least one hollow implant in the heart wall includes placing the at least one hollow implant in the heart wall between the heart chamber and a coronary artery.

11. The method of claim 1, wherein placing the at least one hollow implant in the heart wall includes placing the at least one hollow implant in the heart wall between a left ventricle and a coronary artery.

12. The method of claim 1, wherein the at least one hollow implant is adapted to permit blood to flow from the heart chamber to the blood vessel when the blood flow through the at least one hollow implant is not at least partially obstructed.

13. The method of claim 1, wherein the cardiac tissue includes the heart wall.

14. The method of claim 13, further comprising permitting portions of the heart wall proximate the implant to come together during diastole to at least partially obstruct blood flow through the at least one hollow implant.

15. The method of claim 13, further comprising permitting free portions of the heart wall to come together during diastole to at least partially obstruct the blood flow through the at least one hollow implant.

16. The method of claim 1, further comprising forming at least one irregular surface in the heart wall proximate the passage.

17. The method of claim 16, wherein forming the at least one irregular surface in the heart wall includes one of cutting, lasing, and ablating the heart wall.

18. The method of claim 16, wherein the blood flow through the at least one hollow implant is at least partially obstructed in response to movement of the at least one irregular surface during diastole.

19. The method of claim 1, wherein the blood flow through the at least one hollow implant is fully obstructed in response to movement of the cardiac tissue during diastole.

20. A method of treating a heart, the method comprising:
providing at least one hollow implant defining a lumen, the at least one hollow implant being configured to be positioned in a heart wall between a heart chamber and a coronary vessel, wherein, when the at least one hollow implant is positioned in the heart wall, the lumen at least partially defines a blood flow passage between the heart chamber and the coronary vessel, and wherein the passage is at least partially closable by cardiac tissue entering the passage so as to at least partially obstruct blood flow therethrough during at least a portion of a cardiac cycle;
placing the at least one hollow implant in a heart wall between a heart chamber and a blood vessel; and
during at least a portion of a cardiac cycle, at least partially obstructing blood flow through the at least one hollow implant with cardiac tissue.

21. The method of claim 20, wherein providing the at least one hollow implant includes providing a hollow tube.

22. The method of claim 20, wherein providing the at least one hollow implant includes placing providing a conduit.

23. The method of claim 20, wherein providing the at least one hollow implant includes providing a stent.

24. The method of claim 20, wherein providing the at least one hollow implant includes providing two hollow implants.

25. The method of claim 24, wherein placing two hollow implants in the heart wall includes placing the hollow implants in the heart wall such that they are separated from each other.

26. The method of claim 25, wherein a length of each of the hollow implants is less than a thickness of the heart wall.

27. The method of claim 20, further comprising permitting blood flow through the at least one hollow implant during systole.

28. The method of claim 20, wherein placing the at least one hollow implant in the heart wall includes placing the at least one hollow implant in the heart wall between a left ventricle and the blood vessel.

29. The method of claim 20, wherein placing the at least one hollow implant in the heart wall includes placing the at least one hollow implant in the heart wall between the heart chamber and a coronary artery.

30. The method of claim 20, wherein placing the at least one hollow implant in the heart wall includes placing the at least one hollow implant in the heart wall between a left ventricle and a coronary artery.

31. The method of claim 30, wherein the at least one hollow implant is adapted to permit blood to flow from the left ventricle to the coronary artery when the blood flow through the at least one hollow implant is not at least partially obstructed.

32. The method of claim 20, wherein the cardiac tissue includes the heart wall.

33. The method of claim 32, wherein portions of the heart wall proximate the implant come together during diastole to at least partially obstruct blood flow through the at least one hollow implant.

34. The method of claim 32, wherein free portions of the heart wall come together during at least a portion of the cardiac cycle to at least partially obstruct the blood flow through the at least one hollow implant.

35. The method of claim 20, further comprising forming at least one irregular surface in the heart wall proximate the passage.

36. The method of claim 35, wherein forming the at least one irregular surface in the heart wall includes one of cutting, lasing, and ablating the heart wall.

37. The method of claim 35, wherein the at least one irregular surface at least partially obstructs the blood flow through the at least one hollow implant during at least a portion of the cardiac cycle.

38. The method of claim 20, wherein at least partially obstructing the blood flow through the at least one hollow implant with the cardiac tissue includes fully obstructing the blood flow through the at least one hollow implant with the cardiac tissue.

39. The method of claim 20, wherein the blood flow through the at least one hollow implant is at least partially obstructed during diastole.

40. A method for treating a heart, comprising:
positioning a hollow implant in a heart wall between a heart chamber and a coronary vessel so as to support a blood flow passage between the heart chamber and the coronary vessel, the hollow implant having an interior wall surface defining a lumen; and moving portions of the interior wall surface relative to each other such that, during diastole, the portions reduce a cross-sectional area of the lumen so as to at least partially obstruct blood flow through the implant.

41. The method of claim 40, wherein the hollow implant is configured such that, when positioned in the heart wall, the lumen has a greater cross-sectional area during systole than during diastole at a location of the portions.

42. The method of claim 40, wherein the hollow implant includes a hollow tube.

43. The method of claim 40, wherein the hollow implant includes a stent.

44. The method of claim 40, wherein positioning the hollow implant includes positioning the hollow implant in the heart wall between a left ventricle and a blood vessel.

45. The method of claim 40, wherein positioning the hollow implant includes positioning the hollow implant in the heart wall between the heart chamber and a coronary artery.

46. The method of claim 40, wherein positioning the hollow implant includes positioning the hollow implant in the heart wall between a left ventricle and a coronary artery.

47. The method of claim 40, further comprising biasing the portions of the interior wall surface toward each other during diastole via a mechanism positioned within the wall of the conduit.

48. The method of claim 47, wherein the mechanism is chosen from springs, inflatable structures, and means responsive to electrical and/or mechanical signals.

49. The method of claim 47, wherein the mechanism is configured to permit the interior wall surface portions to move away from each other during systole.

50. The method of claim 40, wherein other portions of the interior wall surface are substantially immovable such that, during the cardiac cycle, the other portions maintain a substantially constant cross-sectional area of the lumen.

* * * * *